United States Patent
Mailland (10) Patent No.: US 8,318,214 B2
(45) Date of Patent: Nov. 27, 2012

(54) METHOD FOR TREATING ONYCHOSCHIZIA

(75) Inventor: Federico Mailland, Milan (IT)

(73) Assignee: Polichem S.A., Luxembourg (LU)

( * ) Notice: Subject to any disclaimer, the term of this patent is extended or adjusted under 35 U.S.C. 154(b) by 357 days.

(21) Appl. No.: 12/659,140

(22) Filed: Feb. 26, 2010

(65) Prior Publication Data

US 2010/0215780 A1 Aug. 26, 2010

Related U.S. Application Data

(63) Continuation-in-part of application No. 10/559,794, filed as application No. PCT/EP2004/006549 on Jun. 15, 2004, now abandoned.

(30) Foreign Application Priority Data

Jun. 23, 2003 (EP) .................................. 03076934

(51) Int. Cl.
*A61K 36/00* (2006.01)
(52) U.S. Cl. ......................................... 424/725; 514/54
(58) Field of Classification Search .................. None
See application file for complete search history.

(56) References Cited

U.S. PATENT DOCUMENTS

| | | | |
|---|---|---|---|
| 5,133,958 A * | 7/1992 | Stuckler | 424/61 |
| 5,478,579 A * | 12/1995 | Sawruk | 424/535 |
| 5,667,768 A | 9/1997 | Ramin | 424/61 |
| 6,027,402 A * | 2/2000 | Oliver | 451/533 |
| 6,919,076 B1 | 7/2005 | Green et al. | 424/94.5 |
| 7,033,578 B2 | 4/2006 | Milland | 424/61 |
| 2002/0028257 A1 * | 3/2002 | Catalfo et al. | 424/727 |
| 2002/0068099 A1 * | 6/2002 | Koniger | 424/725 |
| 2003/0114324 A1 | 6/2003 | Lange | |
| 2004/0013622 A1 | 1/2004 | Godbout | 424/61 |

FOREIGN PATENT DOCUMENTS

| | | |
|---|---|---|
| DE | 198 26 943 C1 | 11/1999 |
| EP | 1 275 371 A1 | 1/2003 |
| JP | 07-285830 | 10/1995 |
| RU | 2083224 C1 | 10/1997 |
| RU | 2140264 C1 | 10/1999 |
| WO | WO 94/25041 | 11/1994 |
| WO | WO 98/48768 | 11/1998 |
| WO | WO 00/03679 | 1/2000 |

OTHER PUBLICATIONS

PROMT Newsletter entitled "Nutrilife Introduces a New Natural Supplement for Beautiful and Healthy Hair, Skin and Nails"; *PR Newswire*, pp. 6577 (2 pgs), Apr. 7, 2000.
PDR® for Herbal Medicines, "Equissetum arvense"; *Medical Economics Company*; First Edition pp. 830-831 (1998).
Trimulyadi et al; "Study of solvent composition on formation of chitosan film forming for nail polish"; *Conference of the Asian Societies of cosmetic Chemists Proceedings Book*; 2001:340 (abstract only).
DE 19826953 C1; "Production of chitin and chitosan biopolymers useful in cosmetic and pharmaceutical preparations and washing, rinsing and cleaning products"; 1999-612155 (abstract).
Derwent Publications Ltd., "Method for Manufacturing Health Food"; Abstr., Apr. 6, 2001 (XP-002253668).
Patent Abstracts of Japan, Publ. No. 072785830; "Care Composition to be Applied to Nail"; L'Oreal SA; Inventor: Ramin Roland (Oct. 31, 1995).

* cited by examiner

*Primary Examiner* — Christopher R. Tate
(74) *Attorney, Agent, or Firm* — Nixon & Vanderhye (57) ABSTRACT

Method for the treatment of onychoschizia in a patient having onychoschizia. The method is performed by administering to the patient a topical composition including (a) at least one herb extract from the genus *Equisetum*, and (b) at least one water-soluble film forming agent which is a derivative of chitosan.

30 Claims, 2 Drawing Sheets

METHOD FOR TREATING ONYCHOSCHIZIA

This application is a Continuation-in-Part of U.S. application Ser. No. 10/559,794 filed 8 Dec. 2005, now abandoned; which is a 371 of PCT/EP04/06549, filed 15 Jun. 2004, the entire contents each of which are hereby incorporated by reference.

The present invention relates to a method for treating onychoschizia, which is a specific alteration of the ungual structure, characterized by lamellar splitting of the nail plate; the method comprises administering to the patient a composition comprising at least a herb from the genus *Equisetum* and one film forming agent.

The strength and physical character of the nail plate is attributable to both its constituents and design. The features of design worthy of note are the double curvature, in transverse and longitudinal axes, and the flexibility of the ventral plate compared to the dorsal aspect. The first one provides rigidity, whereas the latter allows moderate flexion deformity and slightly less extension. The most proximal component of the matrix provides the corneocytes of the dorsal nail surface. These usually provide a shiny surface. When the matrix is altered by disease or the nail surface is subject to trauma, this shine is lost.

It is well known that nail tensile, flexural and tearing strength change with age, sex and the digit from which the nail derived. The nail is 1000 times more permeable to water than the skin, and consequently the nail structure reacts to prolonged or repeated contact with water. Immersion of the nail in water for an hour increases its weight by over 20%, moreover it renders the nail more flexible. After 2 hours, the flexibility is still increasing, while the water content does no more increase. The analysis of in vivo nail by Raman spectroscopy suggests that after soaking in water for 10 minutes, the α-helical protein conformation of the distal nail is made more loose, with greater spacing between proteins as water occupies the interstices. Proximal nail, on the contrary, is still manifesting a high degree of hydration before immersion.

Onychoschizia is a widespread condition that affects mainly housewives, workmen and workwomen, dressmakers, nurses, but also employees.

Longitudinal grooves represent long-lasting conditions that can occur physiologically as shallow and delicate furrows, usually parallel and separated by low, projecting ridges. They become more prominent with age and in certain pathological conditions.

Longitudinal ridges are small rectilinear projections that extend from the proximal nail fold until the free edge of the nail, or may stop shorter. Oblique lines (chevron lines) are more common in children than in adults and their significance is still debatable.

Transverse lines in form of sulci, limited proximally by slightly elevated ridges and affecting the surface of all nails at the corresponding level, have been described as retrospective indicators of a number of pathological status. They reflect a temporary reduction in nail matrix activity.

Lamellar splitting (onychoschizia) is a condition found in 27-35% of normal adult women. The distal portion of the nail splits horizontally in this condition. The nail is formed in layers analogous to the formation of scales in the skin: the thin lamellae then break off. Exogenous factors contribute to the defect. It is common in people who carry out a great deal of housework, whose nails are repeatedly soaked in water and then dried.

Changes in the fingernails of old people are mostly related to diminished tissue repair and inflammatory or degenerative changes of the distal interphalangeal joint. These influences are associated with reduced rate of longitudinal nail growth, thinning of the nail plate and accentuation of longitudinal ridges.

Variations in thickness and consistency of the toenails occur in elderly and are mostly attributable to changes in peripheral circulation.

Healthy looking nails should be smooth, curved, void of any spotting, and should not have any hollows or ridges. Nails in bad conditions can be very harmful for the personal image, if neglected can cause chronic infections, associated to long-lasting embarrassment and pain. Noteworthy, they may be considered a social problem and/or a professional illness.

Repetitive and prolonged wetting and drying of the fingernails is the single most common cause of splitting and ridges of the nails. Splitting of the nails is rarely caused by internal disease or vitamin deficiency, nail polish remover causes onychoschizia (lamellar splitting), finally trauma to the fingers contributes to onychoschizia.

Among the cosmetic damages of the nails, the following can be included: breaking, splitting, fracturing, brittleness, white spots or ridges, poor nail growth, color or shape changes.

Mineral oil has no effect on flexibility, although it can act to maintain some of the flexibility imbued by water. This principle is applied in the treatment of onychoschizia, where repeated hydration and drying of the nail plate results in splitting at the free edge. Splitting can be partially overcome by applications of emollients after soaking the nails in water. The use of a nail varnish, normally a water insoluble polyvinyl resin film, can also decrease water loss: the disadvantage of that procedure is that the removal of the nail varnish by an organic solvent can further damage the nail structure by increasing lamellar splitting.

It is therefore the object of the present invention to provide a nail topical formulation which overcomes the above noted disadvantages, which can be easily formulated, prepared and stored and provides good nail restructuring, hardening and strengthening effect.

DESCRIPTION OF THE INVENTION

The object of the present invention is to provide a novel method for treating onychoschizia, which comprises administering to the patient a nail topical formulation comprising
   a) at least one herb extract from the genus *Equisetum*,
   b) at least one film forming agent.

Moreover, according to the present invention, the nail topical formulation may be in the form of varnish, cream, gel, lotion or foam.

The composition in accordance to the present invention comprises as a component a) at least one herb extract from the genus *Equisetum*. The herb extract may be selected from any known species belonging to the genus *Equisetum*, moreover it may be a dry extract, or an alcoholic extract, or an hydro alcoholic extract, or a glycolic extract. Examples include:
   *Equisetum arvense* in form of plant or part of plant, juice, dry extract, hydro alcoholic extract or glycolic extract
   *Equisetum hiemale* in form of plant or part of plant, juice, dry extract, hydro alcoholic extract or glycolic extract
   The herb extract is preferably selected from *Equisetum arvense*.

The herb extract may be used alone or may be a mixture of different extracts. The preferred amount of component a) in the composition is in the range of 0.1 to 15 wt. %, more preferably 0.3 to 15 wt. %, most preferably 0.5 to 10 wt. % by weight of the total composition.

The composition in accordance to the present invention also comprises as a component b) at least one film forming agent, preferably a water soluble film forming agent. The water soluble film forming agent may be selected from any water soluble film forming agent known in the art. Film forming agents are by definition (see e.g. DIN 55945 (12/1988)) components of a binder which are essential for forming a film, i.e. a thin layer or cover.

The term "water soluble" means in this context that the film forming agent is fully compatible with water so that at 20° C. one part of the film forming agent is soluble in 100 parts or less, preferably 50 parts or less, more preferably 30 parts or less, most preferably 10 parts or less of water.

Due to the presence of a water soluble film forming agent the use of a wide variety of agents is possible, ensuring, thus, an easy application of the drug and simplifying also the storage of the formulation. Since the film forming agent may be used with a wide variety of solvents, the formulation can be chosen in a way that the nail topical formulation composition in accordance with the present invention does not burn nor cause irritation and is easily removable without the use of organic solvents. Furthermore, the water soluble film forming agent used in the composition according to the present invention provides a non-glossy, non-sticky and very plastic film which possesses a matte and natural look favored by both women and men.

As the film forming agent used in accordance to the present invention typically macromolecular compounds of synthetic or natural origin can be used, which are water soluble or have been derivatized by functional groups in order to impart water solubility. Preferably, water soluble derivatives of naturally occurring polymers or derivatives of naturally occurring polymers are employed. It is particularly preferred to use water soluble derivatives of chitosan, the latter being the deacylation product of chitin and being itself water insoluble. Chitin is a natural substance constituting, for example, the carapace of crustaceans and many insects.

Particularly suitable are hydroxyalkyl chitosans and carboxyalkyl chitosans. Hydroxyalkyl chitosans include chitosans which are derivatized with $C_{1-6}$ alkyl groups possessing 1 to 3 hydroxy groups. As an example, hydroxypropyl chitosan can be mentioned. Carboxyalkyl chitosans include chitosans which are derivatized with alkyl groups possessing 1 to 3 hydroxy groups. As an example, carboxymethyl chitosan can be mentioned.

The water soluble film forming agent (component b)) can be used in an amount as long as the formation of a film of the claimed composition can be provided. Typically, the amount of the component b) is in the range of 0.1 to 10 wt. %, more preferably 0.3 to 8 wt. %, most preferably 0.5 to 5 wt. % by weight of the total composition.

The composition in accordance with the present invention further comprises usually as a component c) at least one physiologically acceptable carrier, preferably a solvent.

The solvent is typically a water based solvent in order to avoid a frequent and repeated exposure of the nails and the adjacent skin to aggressive organic solvents. Thus, the physiologically acceptable solvent includes water and mixtures of water with co-solvents.

The co-solvent which can be used in combination with water in the composition in accordance with the present invention is not particularly critical but is selected from the usual physiologically safe organic solvents known in the art. Typically, the co-solvent is a hydrophilic solvent and it is preferably selected from alcohols.

Suitable alcohols are branched or linear alcohols having 1 to 3 hydroxy groups and 2 to 6 carbon atoms whereby the hydroxy groups may be partially converted to ethers. Particularly suitable alcohols are ethanol, 1-propanol, 2-propanol (isopropanol). Particularly suitable are ethanol or isopropanol. Preferably, the total amount of co-solvent used in combination with water present in the composition in accordance with the present invention is sufficient volatile to provide acceptable drying times of the nail topical formulation. Usual drying times, i.e. the time taken to be dry by touch, are less than about five minutes, preferably less than about two minutes.

When water is used in combination with one or more co-solvents, it is important that the individual solvents are compatible with each other and form a clear solution which is stable against phase separation over time. Moreover, the solvent systems used in accordance with the present invention should not only provide uniform evaporation rates and good stability but also enable good flow viscosity characteristics in order to ease the application of the nail topical formulation.

The at least one physiologically acceptable solvent (component c)) is usually employed in an amount suitable in order to impart the above noted properties. It is preferred that the component c) is present in the composition in accordance with the present invention in an amount of 40 to 99.8 wt. %, more preferably 60 to 99 wt. %, most preferably 80 to 95 wt. % by weight of the total composition. The water content in component c) is typically 15 to 70 wt. %, preferably 30 to 65 wt. % by weight of component c) in order to impart the desired properties. Consequently, the co-solvent used in combination with water is typically present in an amount of 30 to 85 wt. %, preferably 35 to 70 wt. % by weight of component c) in order to impart the above noted properties.

The composition according to the present invention may further contain other active agents besides the *Equisetum* herb extract, e.g. sulfur donors, antimycotic agents, antibiotic agents, anti-inflammatory agents, antiseptic agents and/or local anaesthetic agents.

Sulfur donors may interact with the formation and/or the reconstruction process of the nail keratin.

Examples of sulfur donors that may be included in the composition according to the present invention include sulphated amino acids and derivatives, 1-methionine, 1-cysteine, 1-cystine, taurine, 4-thiazolidinecarboxylic acid, methyl sulphonylmethane.

These agents may be used in the respective amounts customary in the art. They are usually employed in an amount from 0.1 to 20 wt. %, preferably from 0.2 to 10 wt. %.

Examples of antimycotic agents that may be included in the composition according to the present invention are imidazole derivatives and their salts; triazole derivatives and their salts; pyridone derivatives like ciclopirox, octopirox and their salts; polyene derivatives and their salts; allylamine derivatives like terbinafine and their salts; morpholine derivatives like amorolfine and their salts; bromsalan derivatives and their salts; nystatin and related compounds; griseofulvin and related compounds; chlorphenesin and related compounds; clodantoin and related compounds; undecylenic acid and its salts and the antimycotic agents disclosed in WO 02/07863A1.

These agents may be used in the respective amounts customary in the art. They are usually employed in an amount from 0.1 to 15 wt. %.

Examples of antibiotic agents which may be listed in the composition in accordance with the present invention include aminoglycosides and their salts; antimycobacterials and their salts; cephalosporins and related beta lactams and their salts; chloramphenicol and related compounds; glycopeptides and their salts; fusidane derivatives and their salts; lincosamides and their salts; macrolides and their salts; mupirocin and related compounds; nitrofuran derivatives and their salts; oxazolidinone derivatives and their salts; penicillins and their salts; phosphonic acid derivatives and their salts; polimixins and their salts; polypeptide antibacterials and related compounds; quinolones and their salts; sulfonamides and diaminopyrimidines and their salts; tetracyclines and their salts.

These antibiotic agents may be used in the respective amounts customary in the art. The antibiotic agents are usually employed in an amount from 0.1 to 10 wt. %.

The anti-inflammatory agent which may be used in the composition in accordance with the present invention include steroidal and nonsteroidal anti-inflammatory agents.

Examples of steroidal anti-inflammatory agents include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, budesonide, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g. acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivates thereof, e.g. acetonide, benetonide, diacetate, hexacetonide.

Examples of nonsteroidal antiinflammatory agents include acetylsalicylic acid, buthylpyrazolidines and their salts; acetic acid derivatives and their salts; oxicam derivatives and their salts; propionic acid derivatives and their salts; phenamates and their salts; coxibs and their salts; nimesulide and related compounds.

These antiinflammatory agents may be used in the respective amounts customary in the art. The anti-inflammatory agents are usually employed in an amount from 0.1 to 5 wt. %.

Examples of antiseptic agents which may be used in the composition in accordance with the present invention include benzalkoniumchlorid, benzethoniumchlorid, cetrimoniumbromid, chlorhexidin, dequaliniumchlorid, triclocarban, triclosan, salicylic acid, benzoic acid sorbic acid and their salts, p-hydroxybenzoic acid and its esters.

These antiseptic agents may be used in the respective amounts customary in the art. The antiseptic agents are usually employed in an amount from 0.01 to 5 wt. %.

Examples of local anaesthetic agents which may be used in the composition in accordance with the present invention include benzocaine, butamben and its picrate, piperocaine hydrochloride, oxybuprocaine hydrochloride, tetracaine hydrochloride, lidocaine hydrochloride, cinchocaine hydrochloride, oxetacaine, propiocaine hydrochloride, bupivacaine hydrochloride, mepivacaine hydrochloride, dyclonine hydrochloride, fomocaine hydrochloride, quinisocaine hydrochloride, polydocanol and benzyl alcohol.

These local anaesthetic agents may be used in the respective amounts customary in the art. The local anaesthetic agents are usually employed in an amount from 0.3 to 10 wt. %.

In addition, the composition in accordance with the present invention may contain other conventional additives customarily present in cosmetic or medicinal nail lacquers, in particular penetration enhancers. Penetration enhancers include any compound known in the art which can enhance the penetration of the pharmacologically active compound through the skin or through the nail. In other words, the penetration enhancer improves the deep diffusion of the drug. Suitable penetration enhancers include salycilic acid, urea, monothioglycerol, N-acethylcysteine, ethyl acetate, dimethyl sulphoxide (DMSO), dimethylacetamide and the penetration enhancers disclosed in WO 99/39680.

The penetration enhancers may be used in an amount of 0 to 10 wt. %, preferably 0.1 to 8 wt. %, most preferably 1 to 5 wt. % by weight of the total composition.

Other conventional additives customarily present in cosmetic or medicinal nail formulations may include sedimentation retarders, chelating agents, antioxidants, silicates, aroma substances, wetting agents, lanolin derivates, light stabilizers and antibacterial substances.

The composition in accordance to the present invention may be prepared according to typical procedures normally employed in the formulation field for liquid preparations, like solutions, nail varnish, lotion or foam, or for semi-solid preparations, like cream or gel. For liquid preparations, the at least one herb extract from the genus *Equisetum* and the at least one water soluble film forming agent may be brought into contact with a solvent or a mixture of solvents and other liquid components either simultaneously or separately by normal mixing techniques. No particular order of addition of the respective ingredients is required. It is preferred to provide stirring in order to ensure complete dissolution of the ingredients. If any of the ingredients is in the solid form, it is particularly preferred to add such an ingredient gradually to the liquid components in order to prevent clumping.

For semi-solid preparations, the at least one herb extract from the genus *Equisetum* and the at least one water soluble film forming agent may be mixed with suitable excipients, like solvents, emulsifyiers, surfactants and/or stiffening agents, either simultaneously or separately by normal mixing techniques. It is preferred to provide stirring under heating and surcharge the solvent in order to avoid losses of evaporation.

The composition in accordance with the present invention is applied as a film or as a thin layer on the nail surface in order to prevent and/or treat onychoschizia, which is a specific alteration of the ungual structure characterized by splitting of the two laminae of the nail plate. Usually, the composition will be applied repeatedly over a period of several weeks or months, depending on the ungual status. Generally the applied composition will contain sufficient active principle to be diffused into the nail so that the application should be repeated only once or twice per day in order to ensure its effectiveness.

The preferred film forming agents of the present invention show a surprising potentiating effect when employed with *Equisetum* herb extracts. This effect is particularly pronounced with hydroxyalkyl chitosans and carboxyalkyl chitosans.

While the film forming agents themselves do not show any hardening or reconstructing effect of the nails when tested in appropriate systems, the effect of the *Equisetum* itself is enhanced when employed in combination with the film forming agents in the present invention.

The composition of the present invention and its use as a nail restructuring and hardening formulation is illustrated, but not limited to, the following examples. All amounts in % are wt. %

EXAMPLE 1

A nail lacquer formulation having the following composition by weight is prepared:

| 1. purified water | 52.5% |
|---|---|
| 2. ethanol | 40.0% |
| 3. *Equisetum* glycolic extract | 5.0% |
| 4. hydroxypropyl chitosan (HPCH) | 1.0% |
| 5. L-methionine | 1.0% |
| 6. diethyleneglycol monomethylether | 0.5% |

The formulation was prepared by using a suitable closed vessel provided with a stirrer. To this vessel were added ethanol, deionized water and diethyleneglycol-monomethylether to form a mixture. Thereafter, after dissolution thereof, *Equisetum arvense* glycolic extract and L-methionine were added. Finally, hydroxypropyl chitosan was added and the resulting mixture was stirred for 24 hours or until dissolution.

The obtained nail lacquer composition had a clear and homogeneous appearance and a yellowish color even after prolonged storage. Moreover, the lacquer was able to form a matte, non-sticky and plastic film which could strongly adhere to the nails. When applied, the moisture and air permeable lacquer did not burn or cause irritation on the adjacent skin or the periungual bed.

EXAMPLE 2

A nail lacquer formulation having the following composition by weight is prepared:

| 1. purified water | 50.5% |
|---|---|
| 2. ethanol | 40.0% |
| 3. *Equisetum* glycolic extract | 4.0% |
| 4. aroma cherry | 3.0% |
| 5. hydroxypropyl chitosan (HPCH) | 1.0% |
| 6. 4-thiazolidinecarboxilic acid | 1.0% |
| 7. cetostearyl alcohol | 0.5% |

The formulation was prepared as shown in the Example 1 and the resulting nail lacquer exhibited the same properties as mentioned in Example 1.

EXAMPLE 3

A nail lacquer formulation having the following composition by weight is prepared:

| 1. purified water | 51.0% |
|---|---|
| 2. ethanol | 40.0% |
| 3. *Equisetum* glycolic extract | 5.0% |
| 4. aroma Tropical | 3.0% |
| 5. hydroxypropyl chitosan (HPCH) | 0.5% |
| 6. ethyl acetate | 0.5% |

The formulation was prepared as shown in the Example 1 and the resulting nail lacquer exhibited the same properties as mentioned in Example 1.

EXAMPLE 4

A nail lacquer formulation having the following composition by weight is prepared:

| 1. purified water | 52.5% |
|---|---|
| 2. ethanol | 40.0% |
| 3. *Equisetum* glycolic extract | 5.0% |
| 4. hydroxypropyl chitosan (HPCH) | 1.0% |
| 5. methylsulphonylmethane | 1.0% |
| 6. diethyleneglycol monomethylether | 0.5% |

The formulation was prepared as shown in the Example 1 and the resulting nail lacquer exhibited the same properties as mentioned in Example 1.

EXAMPLE 5

A nail lacquer formulation having the following composition by weight is prepared:

| 1. purified water | 49.0% |
|---|---|
| 2. ethanol | 40.0% |
| 3. *Equisetum* glycolic extract | 5.0% |
| 4. aroma cherry | 3.0% |
| 5. carboxymethyl chitosan | 1.0% |
| 6. methylsulphonylmethane | 1.0% |
| 7. cetostearyl alcohol | 0.5% |
| 8. ethylacetate | 0.5% |

The formulation was prepared as shown in the Example 1 and the resulting nail lacquer exhibited the same properties as mentioned in Example 1.

EXAMPLE 6

A nail lacquer formulation having the following composition by weight is prepared:

| 1. purified water | 49.0% |
|---|---|
| 2. ethanol | 40.0% |
| 3. *Equisetum* glycolic extract | 5.0% |
| 4. aroma cherry | 3.0% |
| 5. hydroxypropyl chitosan (HPCH) | 1.0% |
| 6. L-methionine | 1.0% |
| 7. diethyleneglycol monomethylether | 0.5% |

The formulation was prepared as shown in the Example 1 and the resulting nail lacquer exhibited the same properties as mentioned in Example 1.

EXAMPLE 7

A cream formulation having the following composition by weight is prepared:

| | |
|---|---|
| 1. purified water | 61.5% |
| 2. cetyl alcohol | 5.5% |
| 3. stearyl alcohol | 5.5% |
| 4. 2-octyldodecanol | 5.5% |
| 5. *Equisetum* glycolic extract | 5.0% |
| 6. coconut fatty acid diethanolamide | 4.0% |
| 7. vaseline album | 3.5% |
| 8. polysorbate 60 | 3.5% |
| 9. light liquid paraffin | 2.5% |
| 10. sorbitanmonostearate | 1.5% |
| 11. hydroxypropyl chitosan (HPCH) | 1.0% |
| 12. benzyl alcohol | 1.0% |

The formulation was prepared by using a suitable stainless steel tank, provided with a thermosetting system and stirrer. To this tank were added cetyl alcohol, stearyl alcohol, 2-octyldodecanol, coconut fatty acid diethanolamide, vaseline album, polysorbate 60, light liquid paraffin, sorbitanmonostearate and benzyl alcohol. The mixture has been heated and maintained at 70-75° C. under stirring conditions. Thereafter, *Equisetum arvense* glycolic extract and hydroxypropyl chitosan were added under stirring. Finally, water was added at 75-80° C. and stirred for 5 minutes. The water was surcharged by 10% to avoid losses of evaporation. Then the mixture was cooled at 28-30° C. and unloaded in a stainless tank.

The obtained cream composition had a clear and homogeneous appearance and a yellowish color even after prolonged storage. When applied on the nails, the cream was able to form a plastic layer which could strongly adhere to the nails, did not burn or cause irritation on the adjacent skin or the periungual bed.

EXAMPLE 8

A foam formulation having the following composition by weight is prepared:

| | |
|---|---|
| 1. propylene glycol | 60.3% |
| 2. purified water | 30.0% |
| 3. *Equisetum* glycolic extract | 5.0% |
| 4. coconut fatty acid diethanolamide | 3.5% |
| 5. hydroxypropyl chitosan (HPCH) | 1.0% |
| 6. trimethylcetylammonium P-toluene sulfonate | 0.2% |

The formulation was prepared by using a suitable stainless steel tank, provided with a stirrer. *Equisetum* extract was dissolved in propylene glycol, then an aqueous solution containing hydroxypropyl chitosan, trimethylacetyl ammonium p-toluenesulfonate and coconut fatty acids diethanolamide were added. The mixture has been maintained at 25-30° C. under stirring conditions.

The above liquid, once put into the vessel equipped with the appropriate device, supplied a soft and persisting foam, which could be spread on the nails providing a matte film that strongly adhered to the nail surface. The same result was achieved by using the above composition with a gaseous propellant at ordinary pressure or a liquid one at high pressure, such as isobutane in a normal pressurized bottle.

EXAMPLE 9

A lotion formulation having the following composition by weight is prepared:

| | |
|---|---|
| 1. polyethylene glycol 400 | 93.89% |
| 2. *Equisetum* glycolic extract | 5.00% |
| 3. hydroxypropyl chitosan (HPCH) | 1.00% |
| 4. lactic acid | 0.10% |
| 5. buthylhydroxyanisole | 0.01% |

The formulation was prepared by using a suitable stainless steel dissolution tank, provided with a stirrer and a heating-cooling jacket. The polyethylene glycol has been heated up to 32-35° C. by forcing vapor through the heating jacket of the dissolution tank. Then, while stirring, the ingredients have been added and dissolved. Upon dissolution, the mixture has been stirred for 3 hours to homogenize.

The above lotion, once put on the nails, provided a matte film that strongly adhered to the nail surface.

EXAMPLE 10

A clinical study was carried out on 36 women with ungual alterations like dystrophy, onycholysis, onychoschizia and ungual brittleness as a result of previous ungual diseases (onychomycosis, psoriasis, bacterial infections) or exogenous causes (chemical agents, trauma, moisture) who volunteered to apply for 28 days a composition obtained by the same method as that indicated in Example 1. The study was randomized, controlled versus no treatment within subjects. The product has been applied monolaterally once daily, preferably on the night, on all the nails of one hand, on the entire nail surface, for 28 consecutive days. The hand to be treated was randomly assigned, the other hand served as the untreated control.

Figure 1:
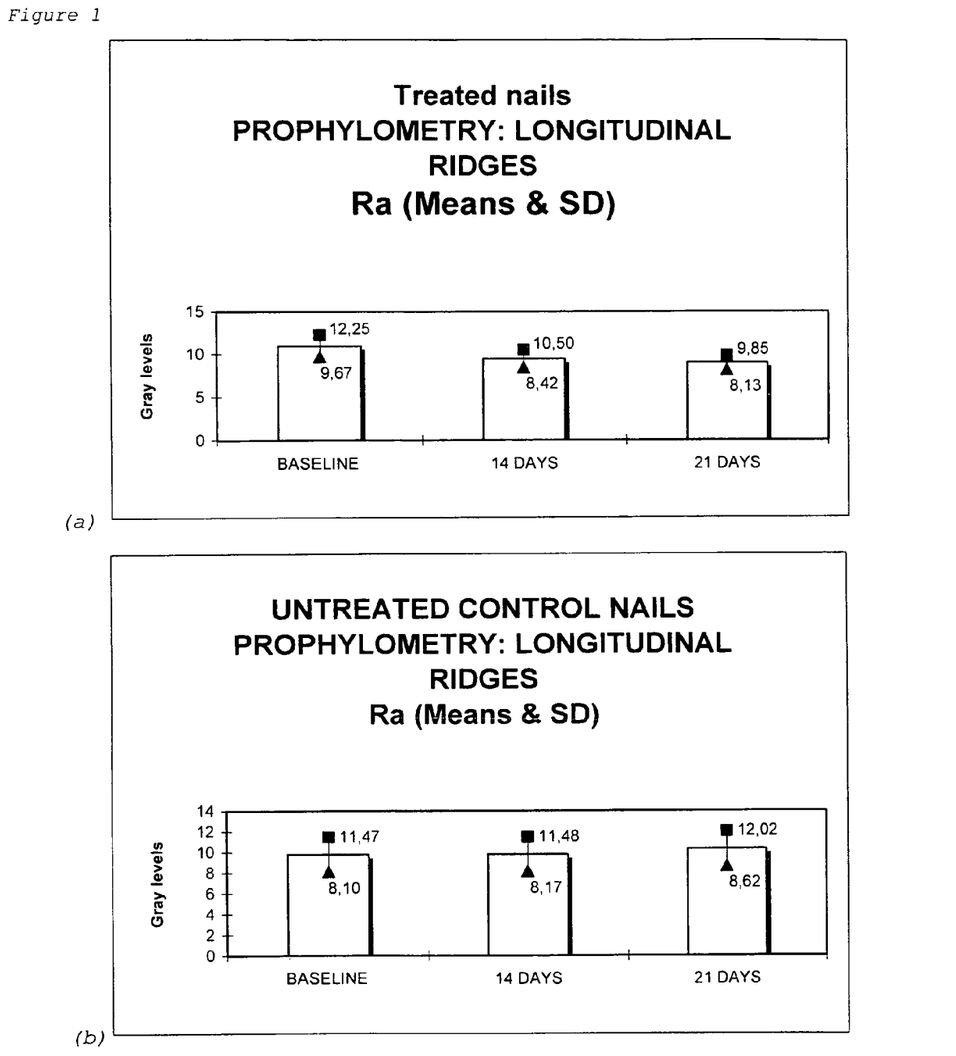
FIG. 1, Prophylometry assessment of longitudinal sulci (a) on treated nails (14 days vs baseline $p<0.01$-21 days vs baseline $p<0.001$); (b) on untreated controls (not significant)

The efficacy parameters according to the protocol have been recorded at baseline and after 14 and 28 days. It included a clinical assessment of the treated and untreated nails and the casts of the thumb nails of both hands, made by silicon resin. The casts have been analyzed by computerized optical prophylometry according to a validated method. The longitudinal ridges have been measured as average roughness score on the nail casts (Ra). The Ra score was $10.96 \pm SD\ 2.58$ at baseline, $9.46 \pm 2.08$ after 14 days and $8.99 \pm 1.72$ after 28 days on the nails treated with the composition according to Example 1. In mean, there was a decrease by 14% at the intermediate evaluation time and a decrease by 18% at the end of application. On the contrary, there was no change of roughness on the untreated nails, whose Ra score were $9.78 \pm 3.37$ at baseline, $9.82 \pm 3.31$ after 14 days and $10.32 \pm 3.4$ at the end of the observation period. The differences of the Ra scores at the end compared to baseline between treated and untreated nails were highly significant ($p<0.001$). The data are summarized in the FIG. 1.

Among the clinical parameters, dystrophy, onycholysis, onychoschizia and ungual brittleness have been measured by a 4-point semi quantitative scale. While there was no change in dystrophy or onycholysis in either group, a definite improvement of both onychoschizia and ungual brittleness was recorded in treated nails, significantly better ($p<0.001$) for both parameters than the results recorded in untreated nails.

The data are summarized in the table 1:

TABLE 1

Clinical parameter assessment of day 21 compared to baseline on treated nails and untreated controls

| Clinical parameter | treated nails | untreated control nails |
|---|---|---|
| onychoschizia | 15% (no change) | 91% (no change) |
| | 70% (1 grade improvement) | 9% (worsened) |
| | 15% (2 grade improvement) | |
| ungual brittleness | 30% (no change) | 94% (no change) |
| | 67% (1 grade improvement) | 3% (1 grade improvement) |
| | 3% (2 grade improvement) | 3% (worsened) |
| dystrophy | 100% (no change) | 100% (no change) |
| onycholysis | 100% (no change) | 100% (no change) |

EXAMPLE 11

A clinical study was carried out on 60 women with onychoschizia and ungual brittleness who volunteered to apply for 4 weeks a composition obtained by the same method as that indicated in Example 1. The study was randomized, controlled, double blind, parallel groups versus:

a composition like that indicated in Example 1, without *Equisetum* herb extract a composition like that indicated in Example 1, without hydroxypropyl chitosan Every subject received one treatment, randomly assigned. The product has been applied on the entire nail surfaces of both hands once daily, preferably on the night, for 4 consecutive weeks.

Figure 2:
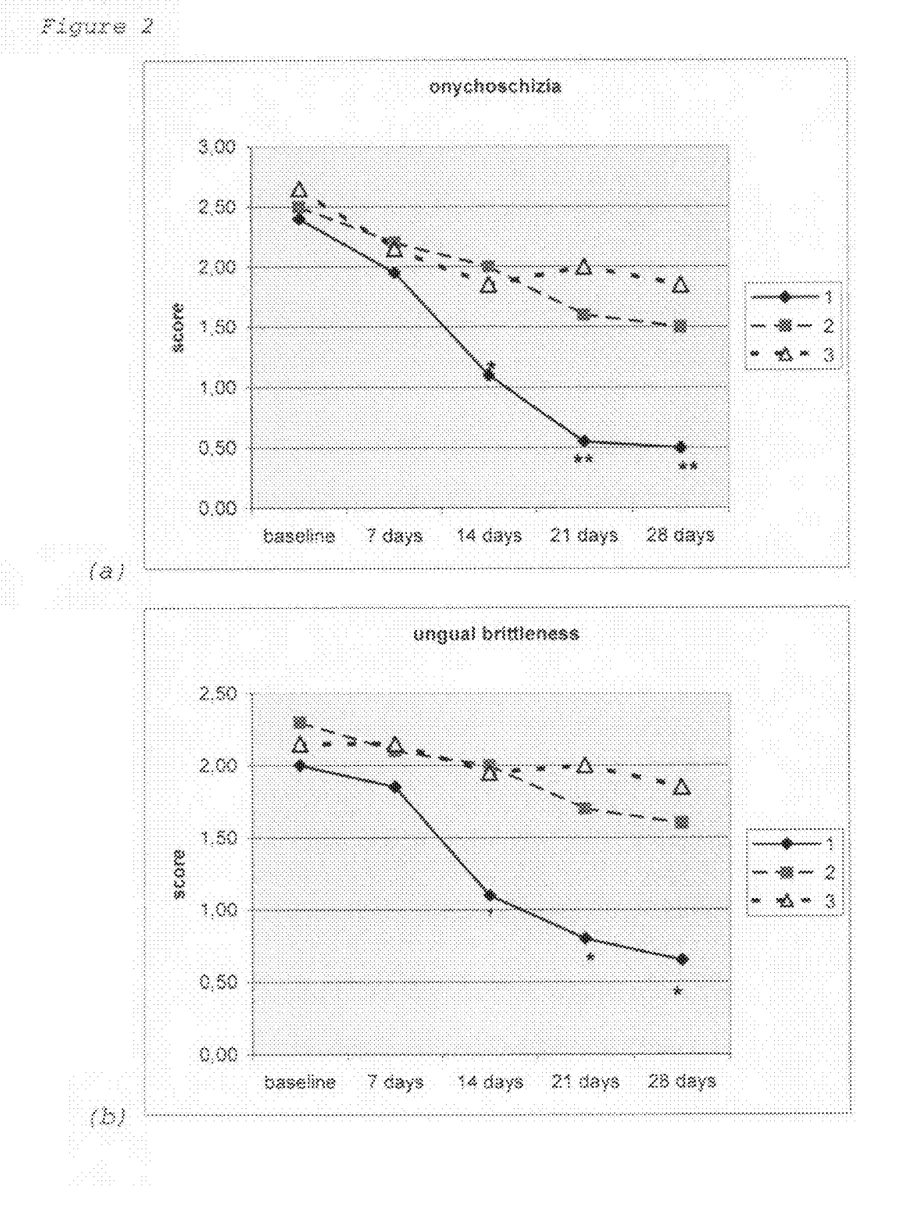
FIG. 2, Time course of onychoschizia (a) and of ungual brittleness (b) during treatment with the composition according to the Example 1 (group 1), a composition like that indicated in Example 1, without hydroxypropyl chitosan (group 2), and a composition like that indicated in Example 1, without *Equisetum* herb extract (group 3). *$p<0.05$; **$p<0.01$ between treatments.

The efficacy parameters according to the protocol have been recorded at baseline and every week. They included a clinical assessment of the nails, measuring onychoschizia and ungual brittleness by means of a 5-point semi quantitative scale from 0=none to 4=very severe. At the end, the subject global impression was also recorded, by means of the following scale: worsened; no change; improvement; recovery. The results have been summarized in the FIG. 2. Definite improvement of both onychoschizia and ungual brittleness was recorded in nails of group 1, treated with the composition obtained by the same method as that indicated in Example 1. The improvement was significantly better of both those recorded in the group 2, who applied a composition like that indicated in Example 1, but different in that hydroxypropyl chitosan was absent and in the group 3, who applied a composition like that indicated in Example 1, but different in that *Equisetum* herb extract was absent.

The subject global impression recorded at the end of the study gave the results reported in table 2:

TABLE 2

Subject global impression after 4 weeks of treatment with the composition according to the Example 1 (group 1), a composition like that indicated in Example 1, without hydroxypropyl chitosan (group 2), and a composition like that indicated in Example 1, without *Equisetum* herb extract (group 3): $p < 0.001$ between group 1 and group 2; $p < 0.001$ between group 1 and group 3.

| Group | worsened n° subjects | no change n° subjects | improvement n° subjects | revovery n° subjects |
|---|---|---|---|---|
| 1 | 0 | 0 | 12 | 8 |
| 2 | 1 | 8 | 11 | 0 |
| 3 | 0 | 14 | 6 | 0 |

EXAMPLE 12

A nail lacquer formulation having the following composition by weight was prepared:

| | |
|---|---|
| 1. Purified water | 52.5% |
| 2. Ethyl Alcohol 96° | 36.5% |
| 3. *Equisetum Arvense* glycolic extract | 5.0% |
| 4. Hydroxypropyl chitosan (HPCH) | 1.0% |
| 5. Methylsulphonyl Methane | 5.0% |
| 6. Diethyleneglycol monoethylether[1] | 0.5% |

[1]Transcutol ® P

The formulation was prepared by using a suitable closed vessel provided with a stirrer. To this vessel were added ethyl alcohol, purified water and diethyleneglycol-monoethylether to form a mixture. Thereafter, after dissolution thereof, *Equisetum arvense* glycolic extract and methylsulphonyl methane were added. Finally, hydroxypropyl chitosan was added and the resulting mixture was stirred for 24 hours or until dissolution.

The obtained nail lacquer composition had a clear and homogeneous appearance and a yellowish color even after prolonged storage. Moreover, the lacquer was able to form a matte, non-sticky and plastic film which could strongly adhere to the nails.

EXAMPLE 13

Comparative

A liquid formulation having the following w/w % composition was prepared:

| | |
|---|---|
| 1. Purified water | 52.5% |
| 2. Ethyl Alcohol 96° | 36.5% |
| 3. *Equisetum Arvense* glycolic extract | 5.0% |
| 4. Chitosan | 1.0% |
| 5. Methylsulphonyl Methane | 5.0% |
| 6. Diethyleneglycol monoethylether[1] | 0.5% |
| 7. glacial acetic acid | q.s. to solubilize chitosan |

[1]Transcutol ® P

Preparation

Chitosan was dissolved in water after acidification with glacial acetic acid at pH 3.0. Then, ethyl alcohol was added and the mix was stirred till to obtain a clear viscous solution. At this point, the pH rose till to 5.5.

Diethyleneglycole monoethyletere, MSM and the glycolic extract were added and mixed till to obtain a clear slightly viscous solution.

The obtained formulation was a clear and yellow-pale solution, homogenous in appearance and slightly viscous.

Once applied to the nails, the lacquer was able to form a matte, non-sticky and plastic film which could strongly adhere to the nails.

EXAMPLE 14

An open, comparative clinical study was performed to assess the activity on onychoschizia (=nail lamellar splitting) of the two topic nail formulations according to the Example 12 and Comparative Example 13, applied daily for four weeks, to the fingernails of subjects with onychoschizia (lamellar splitting of the nail plate). The study was conducted on 34 healthy female volunteers with fingernails affected by onychoschizia, whose informed consent had been obtained, and aged between 20 and 70 years (mean=46). Clinical signs at baseline mainly included lamellar splitting and/or brittle nails, while dystrophy and/or onycholysis were present in few individuals. The extent and severity of nail signs was assessed pre- and post-treatment using the following scale: 0=no; 1=mild; 2=moderate; 3=severe. Nail surface profilometry was assessed by morphometrical analysis of the longitudinal nail grooves on nail casts.

After 4 week-treatment both study products determined a clinical and statistical important reduction of onycoschizia with an high percentage of improved subjects. A statistically significant superiority was demonstrated for the formulation as per the Example 12: in fact, visual score improved at T4 on 74% of volunteers for that formulation, compared to only 52% of volunteers for the formulation as per the Comparative Example 13 (Wilcoxon test p<0.06). Moreover, in the subjects who presented in basal conditions a severe onychoschizia, who represented 35% of included volunteers, at the end of the study severe onychoschizia improved on 80% of subjects for the formulation as per the Example 12 (Dunnett test p<0.05 T0 vs T4) and only on 42% of volunteers for the formulation as per the Comparative Example 13.

Both treatments had a similar effect on rugosity (diminished at the morphometrical analysis of the longitudinal nail grooves) and on nail fragility (improved at the end in the majority of subjects) Therefore, the study confirmed a better effect on the onychoschizia for the formulation as per the Example 12, that was including a water soluble hydroxyalkyl chitosan, compared to the formulation as per the Comparative Example 13, that had the same quali-quantitative composition of all the ingredients, with the exception of chitosan instead of hydroxypropyl chitosan.

EXAMPLE 15

An open, comparative clinical study was performed to assess the activity on onychoschizia of the topic nail formulation according to the Example 12. Twenty-two subjects, 19 females and 3 males, aged 13.6-82.9 years (mean±SD 60.8±16.2) with dystrophy of the fingernails due to chemical aggressives, to trauma or to humidity, were included. Clinical signs included lamellar splitting, brittle or dystrophic nails and/or onycholysis. The nail lacquer according to the Example 12 was randomly applied once daily on the affected fingernails of one hand for an average of 3 months. The other hand served as untreated control. The extent and severity of nail signs was assessed pre- and post-treatment using the following scale: 0=no; 1=mild; 2=moderate; 3=severe.

Mean score of lamellar splitting was in treated hand 1.00±SD 0.82 at baseline and 0.46±0.6 at the end of treatment (p=0.0078). The changes in the untreated hand at the end of the same period were not significant.

Mean dystrophy score was in treated hand 1.32±SD 0.78 at baseline and 0.86±0.71 at the end (p=0.0107). The score did not change significantly in the untreated hand. Mean score of brittle nails was in treated hand 1.18±SD 0.80 at baseline and 0.41±0.59 at the end (p=0.001). In the untreated hand, the score was 1.09±SD 0.75 at baseline and 0.68±0.65 at the end (p=0.0313) (p=0.0352 between treated and untreated nails). Onycholysis was evident in few subjects at baseline and did not change at the end in both treated and untreated nails.

In conclusion, the formulation according to the Example 12 proved to be effective in improving the nail structure in subjects of both genders with onychodystrophy, the effect being particularly evident on lamellar splitting of the nails.

The invention claimed is:

1. A method for the treatment of Onychoschizia in a patient having Onychoschizia, which method comprises applying to the nails of said patient a topical composition comprising:
   a) at least one alcoholic or hydroalcoholic herb extract from the genus *Equisetum*, and
   b) at least one water-soluble film-forming agent, wherein said film-forming agent is a derivative of chitosan selected from the group consisting of hydroalkyl chitosans and carboxyalkyl chitosans;
   wherein component a) is present in an amount of 0.1 to 15% by weight of the total composition, and component b) is present in an amount of 0.1 to 10% by weight of the total composition.

2. Method according to claim 1, wherein said composition comprises c) at least one physiologically acceptable carrier.

3. Method according to claim 1, wherein said composition comprises d) at least one sulfur donor.

4. Method according to claim 1, wherein said alcoholic herb extract is a glycolic extract.

5. Method according to claim 1, wherein said herb extract is a dry extract.

6. Method according to claim 1, wherein component a) is selected from the group consisting of *Equisetum arvense* and *Equisetum hiemale*.

7. Method according to claim 6, wherein component a) is a glycolic extract of *Equisetum arvense*.

8. Method according to claim 1 wherein said hydroxyalkyl chitosans are selected from the group consisting of chitosans which are derivatized with $C_{1-6}$ alkyl groups possessing 1 to 3 hydroxy groups.

9. Method according to claim 8 wherein said hydroxyalkyl chitosan is hydroxypropyl chitosan.

10. Method according to claim 1 wherein said carboxyalkyl chitosans are selected from the group consisting of chitosans which are derivatized with $C_{1-6}$ alkyl groups possessing 1 to 3 carboxy groups.

11. Method according to claim 10 wherein said carboxyalkyl chitosan is carboxymethyl chitosan.

12. Method according to claim 2, wherein the component c) is water or a mixture of water with at least one co-solvent.

13. Method according to claim 12, wherein said co-solvent is an alcohol.

14. Method according to claim 13, wherein said alcohol is a branched or linear alcohol having 1 to 3 hydroxy groups and 2 to 6 carbon atoms.

15. Method according to claim 14, wherein said alcohol is selected from the group consisting of ethanol, 1-propanol and isopropanol.

16. Method according to claim 3, wherein component d) is selected from the group consisting of sulphated amino acids and derivatives thereof, l-methionine, l-cysteine, l-cystine, taurine, 4-thiazolidinecarboxylic acid and methylsulphonylmethane.

17. Method according to claim 1, wherein said composition comprises a compound selected from the group consisting of penetration enhancers, sedimentation retarders, chelating agents, antioxidants, silicates, aroma substances, wetting agents, lanolin derivatives, light stabilizers and antibacterial substances.

18. Method according to claim 1, wherein said composition comprises an additional active agent selected from the group consisting of antimycotic agents, antibiotic agents, anti-inflammatory agents, antiseptic agents and local anesthetic agents.

19. Method according to claim 1, wherein component a) is present in an amount of 0.3 to 15% by weight of the total composition.

20. Method according to claim 19, wherein component a) is present in an amount of 0.5 to 10% by weight of the total composition.

21. Method according to claim 1, wherein component b) is present in an amount of 0.3 to 8% by weight of the total composition.

22. Method according to claim 21, wherein component b) is present in an amount of 0.5 to 5% by weight of the total composition.

23. Method according to claim 2, wherein component c) is present in an amount of 40 to 99.8% by weight of the total composition.

24. Method according to claim 23, wherein component c) is present in an amount of 60 to 99% by weight of the total composition.

25. Method according to claim 24, wherein component c) is present in an amount of 80 to 95% by weight of the total composition.

26. Method according to claim 1, wherein component c) contains water in an amount of 15 to 70% by weight of component c).

27. Method according to claim 26, wherein component c) contains water in an amount of 30 to 65% by weight of component c).

28. Method according to claim 3, wherein component d) is present in an amount from 0.1 to 20% by weight of the total composition.

29. Method according to claim 28, wherein component d) is present in an amount from 0.2 to 10% by weight of the total composition.

30. Method according to claim 1, wherein said composition essentially consists of:
a) the at least one alcoholic or hydroalcoholic herb extract from the genus *Equisetum*
b) the at least one water-soluble film-forming agent,
c) at least one physiologically acceptable carrier,
d) at least one sulfur donor.

* * * * *